United States Patent [19]

Rosenberg et al.

[11] Patent Number: 4,584,316
[45] Date of Patent: Apr. 22, 1986

[54] PALLADIUM ANTI-CANCER COMPLEXES

[75] Inventors: Barnett Rosenberg, Holt, Mich.; Devinder S. Gill, Monroeville, Pa.

[73] Assignee: Research Corporation, New York, N.Y.

[21] Appl. No.: 631,024

[22] Filed: Jul. 16, 1984

Related U.S. Application Data

[63] Continuation of Ser. No. 478,843, Mar. 25, 1983, abandoned.

[51] Int. Cl.$^4$ .................... A01N 55/02; A61K 31/28; C07F 15/00
[52] U.S. Cl. .................... 514/492; 514/277; 556/17; 556/24; 556/28; 556/29; 556/30; 546/2; 544/225; 548/402; 260/239 E
[58] Field of Search ............ 260/429 R, 239 E; 548/101, 107, 402; 546/2; 544/225; 514/477

[56] References Cited

FOREIGN PATENT DOCUMENTS 594449 3/1960 Canada ..................... 260/429 J

OTHER PUBLICATIONS van Kralingen et al, Inorganica Chimica Acta, V36, pp. 69–77 (1979).
Reedijk et al, Chemical Abstracts, 85, 153242k (1976).
Basolo et al, JACS, 82, 4200–4203 (1960).
Chemical Abstracts, 81, 161810b (1974).
Cleare et al, Bioinorg. Chem., 2, 207 (1973).
Hall et al, J. Clin. Hematol. Oncol., 7 (1) 238 (1977).
Appleton et al, Inorg. Chem., 11 (1) 112–117 (1972).
Appleton et al, Inorg. Chem., 9 (8) 1800–1806 (1970).
Chemical Abstracts, vol. 83, 147598y.
Chemical Abstracts, 79, 26673c (1973).
Graham et al, J. Inorg. Nucl. Chem., 41(8) 1245 (1979).
Chemical Abstracts, 91, 67731m (1979).
Vicol et al, J. Inorg. Nucl. Chem., 41 (3) 309 (1979).
Fuetz et al, Inorg. Chem., 20, 1734, 1736–1738 (1981).
MacDougall et al, Inorg. Chemica Acta, 63, 75–83 (1982).

*Primary Examiner*—Helen M. S. Sneed
*Attorney, Agent, or Firm*—Scully, Scott, Murphy & Presser

[57] ABSTRACT

Palladium complexes and pharmaceutical compositions containing palladium complexes adapted for the treatment of tumors cells sensitive to the palladium complexes and methods of treating tumor cells using the palladium complexes are disclosed.

48 Claims, No Drawings

PALLADIUM ANTI-CANCER COMPLEXES

This is a continuation of co-pending application Ser. No. 478,843, filed on Mar. 25, 1983 now abandoned.

The present invention relates to novel palladium complexes and pharmaceutical compositions containing certain palladium complexes adapted for the treatment of tumors and therapeutic methods for the treatment of tumors involving the use of certain palladium complexes.

BACKGROUND OF THE INVENTION

Recently, a number of platinum complexes have been shown by Rosenberg and co-workers to be highly active anti-tumor agents. [U.S. Pat. Nos. 4,177,263 and 4,140,707.] The complex, cis-dichlorodiammine-platinum-II, is the chemotherapeutic agent of choice in the treatment of many and varied tumors.

There are several drawbacks associated with the use of the platinum complexes to treat tumors, however. Generally, the platinum complexes have a relatively low solubility in water thereby rendering it difficult to formulate a composition which can effectively deliver the reagent to the site of the tumor in the body.

Moreover, many of the platinum complexes are highly nephrotoxic thereby further restricting their use in the absence of precautionary measures to avoid damage to the kidneys when administered to animals afflicted with tumors.

Additionally, platinum complexes and cis-dichlorodiammine-platinum-II in particular are relatively inactive against gastro-intestinal tumors, presumably because of an inability to aquate in the presence of the high chloride concentrations present in this region of the body.

It is an object of the present invention to provide certain novel palladium complexes, pharmaceutical compositions comprising certain palladium complexes and methods for the treatment of tumors with certain palladium complexes which do not share the disadvantages associated with the platinum complexes of the prior art.

SUMMARY OF THE INVENTION

According to the present invention there are provided certain novel palladium complexes having the formulas:

$$\text{cis-}Pd(II)A_mX_n \tag{I}$$

wherein:
m is 1 or 2;
n is 1 or 2;
A is selected from the group consisting of bidentate amine ligands excluding ethylenediamine when m is 1 and is a monodentate amine ligand when m is 2; and
X is selected from the group consisting of monovalent anionic ligands excluding chloride when n is 2 and is a divalent anionic ligand when n is 1,
provided that the sum of the valencies of $A_m$ and $X_n$ is four;

$$\text{cis-}Pd(II)(NH_3)_2X \tag{II}$$

wherein:
X is selected from the group consisting of divalent anionic ligands excluding oxalate and malonate;

$$\text{cis-}[Pd(II)A_m(OH)]_xX \tag{III}$$

wherein:
m is 1 or 2;
x is 2, 3 or 4;
A is selected from the group consisting of bidentate amine ligands excluding ethylenediamine when m is 1 and is a monodentate amine ligand when m is 2; and
X represents two monovalent anionic ligands or one divalent anionic ligand when x is 2, three monovalent anionic ligands or one trivalent anionic ligand when x is 3, and four monovalent anionic ligands or two divalent ligands when x is 4; or $$\text{cis-or-trans-}Pd(IV)A_mX_nL \tag{IV}$$

wherein:
m is 1 or 2;
n is 1, 2 or 4;
A is a bidentate amine ligand when m is 1, and two monodentate amine ligands when m is 2;
X is a trivalent anionic ligand when n is 1, a divalent anionic ligand when n is 2 and a monovalent anionic ligand when n is 4;
L represents two monovalent anionic ligands when x is a divalent anionic ligand and one monovalent anionic ligand when x is a trivalent anionic ligand,
provided that the sum of the valencies of $A_m, X_n$ and L is six.

The present invention also provides, in unit dosage form, a pharmaceutical composition adapted for the treatment of animal tumor cells sensitive to the compounds represented by formulas V, VI and VII comprising an anti-tumor effective amount of a pharmaceutically acceptable carrier and a complex having the formula:

$$\text{cis-}Pd(II)A_mX_n \tag{V}$$

wherein:
m is 1 or 2;
n is 1 or 2;
A is a bidentate amine ligand when m is 1 and $NH_3$ or a monodentate amine ligand when m is 2; and
X is a monovalent anionic ligand when n is 2 and a divalent anionic ligand when n is 1,
provided that the sum of the valencies of $A_m$ and $X_n$ is four;

$$\text{cis-}[Pd(II)A_m(OH)]_xX \tag{VI}$$

wherein:
m is 1 or 2;
x is 2, 3, or 4;
A is a bidentate amine ligand when m is 1 and $NH_3$ or a monodentate amine ligand when m is 2, and
X represents two monovalent anionic ligands or one divalent anionic ligand when x is 2, three monovalent anionic ligands or one trivalent anionic ligand when x is 3 and four monovalent anionic ligands or two divalent anionic ligands when x is 4; or $$\text{cis- or trans-}Pd(IV)A_mX_nL \tag{VII}$$

wherein:
m is 1 or 2;
n is 1, 2 or 4;

A is a bidentate amine ligand when m is 1, and two monodentate amine ligands when m is 2;

X is a trivalent anionic ligand when n is 1, a divalent anionic ligand when n is 2 and a monovalent anionic ligand when n is 4;

L represents two monovalent anionic ligands when X is a divalent anionic ligand and one monovalent anionic ligand when X is a trivalent anionic ligand, provided that the sum of the valencies of $A_mX_n$ and L is six.

There is also provided by the present invention a method for the treatment of animal tumor cells sensitive to complexes of the formulas (V), (VI) or (VII) comprising the administration to an animal afflicted with said tumor cells an amount of a complex of formula (V), (VI) or (VII) effective to cause regression of the tumor.

DETAILED DESCRIPTION OF THE INVENTION

It has previously been suggested to employ certain palladium complexes as anti-tumor agents in chemotherapy. However, in all instances reported in the literature the complexes tested had either little or marginal anti-tumor activity. The low activity of the palladium complexes tested heretofore as compared with the related platinum complexes has been attributed to the fast equation of the leaving groups which dissociate from the metal in vivo. See Connors, *Cancer Treatment Reports*, Vol. 63, Sept.-Oct., 1979, pages 1499-1502; Lim et al, *J. Inorg. Nucl. Chem.*, Vol. 38, pages 1911-1914 (1976); Connors, *Platinum Coordination Complexes in Cancer Chemotherapy*, pages 13-37 (Springer-Verlag Berlin, 1974); Cleare, *Bioinorganic Chemistry*, Vol. 2, pages 187-210 (1973); Graham et al, *J. Inorg. Nucl. Chem.*, Vol. 41, pages 1245-1249 (1979); Kirschner et al, *J. Med. Chem.* Vol. 9, pages 369-372 (1966); Kirschner et al, *168th Annual Meet. ACS* (Sept. 1974) (Abstract); Kirschner et al, *Adv. Exp. Med. Biol.*, Vol. 91, 151 (1977); Kirschner et al, *Inorganic and Nutritional Aspects of Cancer*, pages 151-160, Plenum, N.Y. (1978); Kirschner et al, *J. Clin. Hema. and Onc.*, Vol. 7, page 190 (1977).

The novel palladium complexes of the invention and certain other palladium complexes known in the art have been found, however, to have an anit-tumor activity comparable to and, in some instances, greater than the platinum complexes currently in widespread use in cancer chemotherapy.

The palladium complexes of the present invention also find utility as catalysts in methods for the homogeneous hydrogenation, isomerization, hydroformylation and oxidative hydrolysis of olefins; the carboxylation of methanol and the activation of alkanes. The palladium complexes of optically active amines also find utility in stoichiometric and catalytic asymmetric syntheses from prochiral substrates.

In the palladium complexes of the present invention of formulas I, II, III and IV above, and in the known palladium complexes employed in the pharmaceutical composition and therapeutic methods of the invention, the bidentate amine ligands are preferably selected from the group consisting of alkylene diamines (excluding ethylene diamine where indicated), of the formula:

$R_1RN-Alk-NRR_1$ wherein:

R and $R_1$ may be the same of different, and are H, lower alkyl, hydroxy alkyl, lower alkoxy, aryl, arloweralkyl, cycloalkyl, cycloalkenyl and substituted derivatives thereof, and alk is lower alkylene having from 2 to 12 carbon atoms, unsubstituted or substituted by hydroxoalkyl, lower alkoxy, aryl or arloweralkyl; cycloalkanes (which may be substituted by the above groups) having from 3 to 12 carbon atoms, and heterocyclic diamines which may be saturated, unsaturated and unsubstituted or substituted by the above groups.

Suitable bidentate amine ligands include 1,2-diaminopropane, 1,3-diaminopropane, 1,2-diaminocyclohexane, 2,2'-bipyridine, 1,10-phenanthroline; 1,2-diaminoethane; 1,2-diaminobenzene; imidazole; pyrimidine; 3-aminopyridine; 1,4-diaminobutane; 1,2-diaminocyclopentane; o-phenylenediamine; 5,6-diaminopyrimidine; 2,3-diaminonaphthalene; 1,2-diaminocycloheptane; 1,2-diaminocyclooctane; 1,2-diamino-b 2-methyl propane; nitrophenylenediamine; 1,3-diamino-2-propanol; 2,3-diaminopyridine; 3,4-diaminotoluene; 1,2-dianilinoethane; 4-carboxyphenylene diamine; 2-amino-4 picoline; 3-aminoquinoline; 1,5-diaminopentane.

The monodentate amine ligands are preferably selected from the group consisting of: lower alkyl amines; lower alkyl amines substituted in said alkyl group or on said nitrogen atom by an aryl group, a hydroxyloweralkyl group, hydroxy or a lower alkoxy group; aryl amines; heterocyclic amines or amino acids.

Suitable monodentate amine ligands include the lower alkyl amines, e.g., methyl-, ethyl-, n-propyl-isopropyl-, n-butyl amines, etc.; aryl amines, e.g., aniline, etc.; or arloweralkyl amines, e.g., benzyl-amine, etc.; hydroxy lower alkyl amines, e.g., ethanolamine, propanolamine, etc.; lower alkoxyl amines, e.g., methoxylamine, etc.; lower alkoxy, lower alkylamines, e.g.; methoxymethylamine; heterocyclic amines such as pyridine, aziridine, etc.; all amino acids of the formula $R-CHNH_2-COOH$ wherein R is H, lower alkyl (e.g., methyl, isopropyl, etc.), hydroxy lower alkyl (e.g., hydroxymethyl, hydroxyethyl, etc.), or arloweralkyl (e.g., benzyl, etc.).

Suitable monodentate anionic ligands include chloride (except where expressly excluded), bromide, iodide, nitrite, hydroxide, nitrate, lactate, alkoxy, aryloxy hydride, fluoride, acetate, trifluoroacetate, chloroacetate, cyanide, cyanate, thiocyanate, ozonide, azide, chlorite, hypochlorite, hypophosphite.

Suitable bidentate anionic ligands include malonates and oxalates (except where expressly excluded), pyrophosphite, dithiooxalate, phthalate, carboxyphthalate, gluconate, glucuronate, carbonate, sulphite, selenite, pyrosulphite, dithionite, sulphate.

Suitable trivalent anionic ligands include phosphate, arsenite, orthoarsenate, ferricyanide.

Particularly preferred novel palladium complexes are those of formula (I) having the formulae:

$Pd(II)(1,2\text{-diaminocyclohexane})(NO_3)_2$, $Pd(II)(1,2\text{-diaminopropane})(NO_3)_2$,
$Pd(II)(1,3\text{-diaminopropane})(NO_3)_2$,
$Pd(II)(2,2'\text{-bipyridine})(NO_3)_2$, and
$Pd(II)(1,2\text{-diaminoethane})(NO_3)_2$.

and those of the formula III having the formulae:

$[Pd(II)(cis\text{-}1,2\text{-diaminocyclohexane})(OH)]_n [NO_3]_n$ wherein: n=2, 3 or 4.

[Pd(II)(trans-1,2-diaminocyclohexane) (OH)]$_n$ [NO$_3$]$_n$ wherein: n=2, 3 or 4.

It will be understood that all references herein to "lower alkyl" or "lower alkylene" are to alkyl or alkylene groups containing from 2 to 6 carbon atoms, unless otherwise indicated.

The novel palladium complexes of the invention are readily prepared by first forming the chloroaminepalladium complex by reacting a suitable palladium chloride (e.g., sodium tetrachloropalladate (II) in water with a suitable amine. The chloroamine-palladium complex is then reacted with the silver salt of the appropriate anionic ligand. Alternatively, they are prepared from the diaquo complex by the addition of the sodium salt of the anionic ligand in water. The oligomeric complexes are isolated from the monomeric complexes at different pH's. The dicarboxylate complexes were prepared by adding the sodium salt of the dicarboxylic acid to the solution of the anionic complex whereby the dicarboxylate complexes crystallize out of the solution.

The following non-limiting examples are illustrative of methods of preparing the palladium complexes of the invention:

EXAMPLE 1

Preparation of Dichloro(cis-1,2-diaminocyclohexane)palladium 1,2-Diaminocyclohexane (hereinafter-dach) as an isomeric mixture of trans- and cis-dach, respectively, was separated into trans-dach dihydrochloride, and cis-dach sulphate by the method of Saito et al, Chem. Lett., Vol. 123 (1976).

To a solution containing 5.0 g (0.017 mole) of sodium tetrachloropalladate (II) in 200 ml of water buffered with sodium hydroxide (3.604 g (0.017 mole) of cis-dach dihydrochloride was added. The mixture was stirred at room temperature. Within 10 minutes, a yellow precipitate was obtained. The mixture was stirred for another 12 hours. The yellow precipitate was removed by filtration, washed with 0.01N HCl, cold water, hot water, alcohol and ether to give a quantitative yield of the product. This was further purified by treatment with silver nitrate in water and precipitation of the dichloro complex with 1N HCl. Elemental analysis gave: H, 4.84; C, 24.63; N, 9.60; Cl, 24.67; Pd, 36.43. Calculated for H$_{14}$C$_6$N$_2$Cl$_2$Pd: H, 4.81; C, 24.7; N, 9.61; Cl, 24.4; Pd, 36.51.

EXAMPLE 2

Preparation of Dinitrato (cis-1,2-diaminocyclohexane)palladium

A mixture of Pd(cis-dach)Cl$_2$ 5.828 g (0.02 mole) prepared according to Example 1 and silver nitrate 6.664 g (0.0196 mole) in 100 ml of water, acidified to pH 1.5 with nitric acid, was stirred for 24 hours in a low actinic glass flask. Silver chloride was removed by filtration and the pale yellow solution was removed by filtration. The pale yellow solution was concentrated on a flash evaporator and allowed to crystallize. This was crystallized again from acidified nitric acid. Elemental analysis gave: H, 4.13; C, 20.87; N, 16.13; Pd, 30.67. Calculated for H$_{14}$C$_6$N$_4$O$_6$Pd: H, 4.06; C, 20.90; N, 16.26; Pd, 30.89.

EXAMPLE 3

Preparation of oligomeric [(1,2-diaminocyclohexane)palladium] Nitrate

Pd(dach)(NO$_3$)$_2$ (5.0 g) was dissolved in 70 ml water. The pH of the solution was raised to 6.45 by dropwise addition of 1.5N NaOH. The flask was stoppered and allowed to stand at room temperature for 30 minutes. The volume of the solution was reduced to 30 ml on a flash evaporator at 30° C. and the solution was allowed to stand at 5° C. for a week. During this time, the obligomer crystallized out of the solution as a yellow colored complex. The pH of the filtrate was raised to 6.45 again and the above procedure repeated to get more of the trimer. The overall yield of the complex was 60%. The complex analysed as: H, 5.08; C, 23.95; O, 21.42; N, 13.98; Pd, 35.35. Calculated for H$_{45}$C$_{18}$N$_9$O$_{12}$Pd$_3$: H, 5.01; C, 24.05; O, 21.38; N, 14.03; Pd, 35.54.

EXAMPLE 4

Preparation of Tartronato(1,2-diaminocyclohexane)palladium

To a solution containing 1.0332 g (0.003 mole) of dinitratro(dach) palladium was added tartronic acid (1.0 g, 0.0096 mole), neutralized with 2N NaOH. A yellow crystalline precipitate was obtained. This was filtered, washed with ethanol, acetone and dried at room temperature and reduced pressure. The yield was 90%. The complex analyzed as H, 4.79; C, 31.95; N, 8.23; O, 23.54; Pd, 31.28. Calculated for C$_9$H$_{16}$N$_2$O$_5$Pd: H, 4.73; C, 31.91; N, 8.27; O, 23.64; Pd, 31.44.

EXAMPLE 5

Preparation of Dichloro(1,2-diaminoethane)palladium

To a solution, containing 5.0 g of sodium tetrachloropalladate (II), in 200 ml of water, 2.5 g of ethylenediamine hydrochloride was added. The solution was buffered with sodium hydroxide. The mixture was stirred at room temperature and a yellow precipitate was obtained in 10 minutes. Stirring was continued overnight to ensure the completion of the reaction. The yellow precipitate was removed by filtration, washed with 0.1N HCl, cold water alcohol and ether to give a quantitative yield of the product. The complex was further purified by treatment with silver nitrate in water and precipitation of the dichloro complex with hydrochloric acid.

EXAMPLE 6

Preparation of Dinitrato(1,2-diaminoethane)palladium

A mixture of dichloro(1,2-diaminoethane)palladium 3.0 g and silver nitrate 4.2 g in 60 ml of water was stirred for 24 hours in a flask covered with aluminum foil. Silver chloride was removed by filtration and the pale yellow solution was concentrated on a flash evaporator and allowed to crystallize. The complex analyzed as C, 8.33; H, 2.78; N, 19.10; Pd, 36.31. Calculated for C$_2$H$_8$N$_4$O$_6$Pd: C, 8.26; H, 2.75; N, 19.28; Pd; 36.40.

EXAMPLE 7

Preparation of Malonato(1,2-diaminoethane)palladium

Dichloro(1,2-diaminoethane)palladium (1.0 g), silver nitrate (1.4 g) and water (20 ml) were stirred together in a stoppered flask, covered with aluminum foil for a period of 20 hours. Solid silver chloride was removed by filtration and to the filtrate malonic acid (1.0 g in 10 ml of water) neutralized with 2N KOH was added. The mixture was carefully warmed until crystals of the product began to form in greater quantity. The mixture was then cooled to room temperature, allowed to sit overnight at 5° C. and filtered. The filtrate was reheated for 5-10 minutes and cooled at 0° C. to collect a further crop. The product was further crystallized from hot water. Yield: 80%.

EXAMPLE 8
Preparation of Dichloro(1,2-diaminocyclohexane)palladium

To a solution containing 4.0 g of sodium tetrachloropallidate (II) in 160 ml of water, 2.54 g of (mix-dach) dihydrochloride (70:30, trans:cis) was added. The solution was buffered with sodium hydroxide and the mixture was stirred at room temperature for 20 hours. The yellow precipitate was removed by filtration, washed with 0.01N HCl, cold water, hot water, alcohol and ether to give a quantitative yield of the product. The complex was further purified by treatment of the dichloro complex with silver nitrate in water and precipitation of the dichloro complex with hydrochloric acid.

EXAMPLE 9
Preparation of Dinitrato(1,2-diaminocyclohexane)palladium

A mixture of Pd(mix-dach)Cl$_2$ 5.828 g (0.02 mole) and silver nitrate 6.664 g (0.0196 L mole) in 100 ml of water was stirred for 24 hours in a low-actinic flask. Silver chloride was removed by filtration. The pale yellow solution was concentrated on a flash evaporator and allowed to crystallize.

EXAMPLE 10
Preparation of Dichloro(cis-1,2-diaminocyclohexane)palladium

A mixture of sodium tetrachloropalladite (5.0 g) and (cis-dach) H$_2$SO$_4$ (1.39 g) in 160 ml of water was stirred at room temperature for 20 hours. The dichloro complex was removed by filtration; washed with water and acetone and dried. The yield was quantitative.

EXAMPLE 11
Preparation of Dinitrato(cis-1,2-diaminocyclohexane)palladium

A mixture of Pd(cis-dach)Cl$_2$ 5.828 g (0.02 mole) and silver nitrate 6.664 g (0.0106 mole) in 100 ml of water was stirred for 24 hours. Silver chloride was removed by filtration. The yellow solution was concentrated on a flash evaporator and allowed to crystallize. The yield was 75%.

EXAMPLE 12
Preparation of Oxalato(trans-1,2-diaminocyclohexane)palladium

Pd(trans-dach)(NO$_3$)$_2$ (0.55 g) in 40 ml of water and potassium oxalate (0.6 g) in 10 ml of water were mixed together. The mixture was heated to 70° C. to obtain crystals. It was cooled, filtered and dried. Yield: 75%.

EXAMPLE 13
Preparation of Dinitrato(2,2'-bipyridyl)palladium

A mixture of dichloro(2,2'-bipyridyl)palladium (4.0 g) and silver nitrate (3.729 g) in 50 ml of water was stirred for 20 hours. Silver chloride was removed by filtration and the solvent was concentrated to give 92% yield of the complex. It was further crystallized from hot water.

EXAMPLE 14
Preparation of Sulphato(1,2-diaminopropane)palladium

A mixture of silver sulphate (1.684 g) and dichloro(1,2-diaminopropane)palladium (2.0 g) in 30 ml of water was stirred for 20 hours. Silver sulphate was removed by filtration and the filtrate dried under reduced pressure to give 85% yield of the sulphato complex.

EXAMPLE 15
Preparation of Oxalato-bis(cyclohexylamine)palladium

A mixture of K$_2$PdOX$_2$.2H$_2$O (5.52 g, 0.01394 moles) and cyclohexylamine hydrochloride (3.8355 g, 0.02788 mole) was dissolved in 900 ml of water. The mixture was heated to 40° C. and 1.12 g (0.02788 mole) of sodium hydroxide dissolved in 100 ml of water was added dropwise. A pale yellow precipitate of the complex was obtained. It was cooled overnight at 5° C., filtered, washed with water, ethanol and dried.

EXAMPLE 16
Preparation of 1,1-cyclobutanedicarboxylato(trans-1,2-diaminocyclohexane)palladium Dichloro(trans-dach)Pd (1.0 g) was dissolved in 40 ml of water and was added to 1,1-cyclobutanedicarboxylic acid (1.0 g in 10 ml of water); pH of the solution was raised to 5.6 and within five minutes, pale yellow precipitate was obtained which was removed by filtration, washed with alcohol and dried. Yield: 90%.

EXAMPLE 17
Preparation of Dichloro(1,3-diaminopropane)palladium

A mixture of sodium tetrachloropalladite (6.0 g) and 1,2-diaminopropane dihydrochloride (3.0 g) in 150 ml of water was buffered with sodium hydroxide and stirred for 20 hours at room temperature. This gave quantitative yield of the dichloro complex.

EXAMPLE 18
Preparation of Dinitrato(1,3-diaminopropane)palladium

A mixture of the dichloro(1,3-diaminopropane) palladium 3.0 g and silver nitrate 3.976 g in 50 ml of water was stirred for 24 hours. Silver chloride was removed by filtration and the solution was concentrated to give 85% yield of the dinitrato complex.

EXAMPLE 19
Preparation of Dichloro(1,2-diaminopropane)palladium

A mixture of sodium tetrachloropallidate (6.0 g) and 1,2-diaminopropane dihydrochloride (3.0 g) in 150 ml of water, buffered with NaOH, was stirred for 20 hours to give the quantitative yield of the dichloro complex. This was further purified by reaction with silver nitrate in water and precipitation with hydrochloric acid.

EXAMPLE 20

Preparation of Dinitrato(1,2-diaminopropane)palladium

A mixture of the dichloro(1,2-diaminopropane) palladium 3.0 g and silver nitrate 3.976 g in 40 ml of water was stirred for 20 hours. Silver chloride was removed by filtration and the solution was concentrated to give 80% yield of the product. This was further crystallized from water, acidified with nitric acid to prevent hydrolysis. The complex analyzed as: C, 12.38; H, 3.44; N, 17.28; Pd, 34.91. Calculated for $C_3H_{11}N_4O_6Pd$: C, 11.8; 3.6; N, 18.34; Pd, 34.84.

The complexes of the invention as well as those known in the prior art and which possess anti-tumor activity are preferably administered intravenously or intraarterially to those afflicted with tumor cells sensitive to the complexes in solution in suitable i.v. administrable media such as water, 5% dextrose solution, saline solution (varying in NaCl concentrations from 0% to 5× normal saline).

The pharmaceutical compositions may be prepared according to conventional methods well known in the prior art. The appropriate palladium complex may, for example, be dissolved in water at appropriate pH's, filtered, sterilized, dispensed into ampoules, freeze dried and capped with hyperdermic penetrable seals.

The amount of complex included in the pharmaceutical composition of the invention will vary depending in each case upon the anti-tumor activity of the complex, the toxicity and solubility characteristics thereof, etc. Generally, however, an amount of palladium complex ranging from about 10 to 20,000 mg, preferably from about 100 to about 2,000 mg per unit dosage form of the composition may be incorporated therein.

The palladium complexes are preferably administered intravenously or intraarterially, either as a push injection or by a slow drip over a period of hours. This treatment may be repeated each day for a few consecutive days, or given on one day every month. This is repeated for a number of months at dosages in the range of from about 1 to about 200 mg/kg of body weight, preferably from about 1 to about 50 mg/kg of body weight. Again, the particular dosage will depend upon the therapeutic and chemical and physical characteristics of the complex and the nature of the tumor treated as well as the health of the individual afflicted with the tumor.

The following examples illustrate the anti-tumor activity of the palladium complexes.

EXAMPLE 21

Measurements of Anti-Tumor Activity of Palladium Complexes

Animal tests for evaluating anti-tumor activities of palladium complexes were performed on ICR randombred, white, female, 4–5 week old (18–20 g) mice. Ascites Sarcoma-180 J cells ($4 \times 10^6$) were injected intraperitoneally into animals on day 0 and the compounds (6 animals/dose level) were injected as solutions of slurries, on day 1. Evaluations were made on 2× the average day of death of the negative control. 7 mg/kg of cis-Pt(NH$_3$)$_2$Cl$_2$ is injected as a positive control of the testing situation. The % increase Life Span (ILS) is computed as follows: the average day of death of test animals minus the average day of death of the negative controls, divided by the average day of death of controls ×100.

Individual tests of representative complexes are listed in Table 1 below, with the concentration of the drug and % increased life span (% ILS expressed in days).

TABLE 1

| Complex | mg/kg | % ILS |
|---|---|---|
| Pd(dach)(NO$_3$)$_2$ | 20 | 27 |
| | 40 | 27 |
| | 60 | 35 |
| | 80 | 65 |
| [Pd(dach)(OH)]$_n$(NO$_3$)$_n$ | 20 | 2 |
| | 30 | 53 |
| | 50 | 48 |
| | 80 | 75 |
| Pd(dach)malonate | 50 | 62 |
| | 100 | 51 |
| | 150 | 76 |
| | 200 | 46 |
| Pd(trans-dach)(NO$_3$)$_2$ | 30 | 60 |
| | 60 | 84 |
| | 120 | 44 |
| | 140 | −63 |
| Pd(cis-dach)(NO$_3$)$_2$ | 30 | 56 |
| | 60 | 44 |
| | 120 | 56 |
| | 140 | −62 |
| Pd(1,2-propylenediamine)(NO$_3$)$_2$ | 50 | 19 |
| | 100 | 72 |
| | 150 | 54 |
| | 200 | 70 |
| Pd(1,3-diaminopropane)(NO$_3$)$_2$ | 40 | 48 |
| | 60 | 81 |
| | 80 | 55 |
| | 100 | 74 |
| Pd(1,2-diaminoethane)(NO$_3$)$_2$ | 40 | 61 |
| | 60 | 55 |
| | 80 | 94 |
| | 100 | 68 |
| Pd(2,2'-bipyridyl)(NO$_3$)$_2$ | 40 | 57 |
| | 60 | 55 |
| | 80 | 70 |
| | 100 | 61 |
| Pd(NH$_3$)$_2$(NO$_3$)$_2$ | 10 | −23 |
| | 20 | 14 |
| | 40 | 4 |
| Pd(dach)Cl$_2$ | 12.5 | 19 |
| | 25 | −4 |
| | 50 | 20 |
| | 100 | 32 |
| Pd(ethylenediamine)Cl$_2$ | 12.5 | −1 |
| | 25 | −5 |
| | 50 | −12 |
| | 100 | 2 |
| Pd(NH$_3$)$_2$ Cl$_2$ | 12.5 | −7 |
| | 25 | 6 |
| | 50 | 4 |
| | 100 | 11 |

Cis-dichlorodiammineplatinum (II) gives a % ILS 65–80.

The results set forth in Table 1 unequivocally establish the anti-tumor activity of the palladium complexes described herein.

We claim:

1. A palladium complex having the formula cis:

wherein:
m is 1 or 2,
n is 1 or 2, and
when m is 1, A is selected from the group consisting of bipyridine and alkylene diamines other than ethylene diamine having the formula

wherein R and R$_1$ may be the same or different and are H, C$_2$ to C$_6$ alkyl, C$_2$ to C$_6$ hydroxy alkyl, C$_2$ to $C_6$ alkoxy, $C_6$ to $C_{10}$ aryl, $C_3$ to $C_{12}$ cycloalkyl and $C_3$ to $C_{12}$ cycloalkenyl and Alk is selected from the group consisting of unsubstituted $C_2$ to $C_{12}$ alkylene; $C_2$ to $C_{12}$ alkylene substituted with $C_2$ to $C_6$ hydroxy alkyl or $C_2$ to $C_6$ alkoxy; $C_6$ to $C_{10}$ aryl and $C_3$ to $C_{12}$ cycloalkane, when m is 2, A is selected from the group consisting of $C_2$ to $C_6$ alkyl amine; $C_2$ to $C_6$ alkyl amine substituted in the alkyl group or nitrogen atom thereof by $C_2$ to $C_6$ hydroxy alkyl, hydroxy or $C_2$ to $C_6$ alkoxy; aniline; benzylamine and amino acids having the formula $R^3CHNH_2COOH$ wherein $R^3$ is H, $C_2$ to $C_6$ alkyl, $C_2$ to $C_6$ hydroxy alkyl and benzyl, and when n is 2, X is a monovalent anionic ligand selected from the group consisting of bromide, iodide, nitrite, hydroxide, nitrate, lactate, $C_2$ to $C_6$ alkoxy, fluoride, acetate, trifluoracetate, chloroacetate, cyanide, cyanate, ozonide, azide, chlorite, hypochlorite and hypophosphite, and when n is 1, X is a divalent anionic ligand selected from the group consisting of pyrophosphite, dithiooxalate, phthalate, carboxyphthalate, gluconate, glucuronate, carbonate, sulphite, selenite, pyrosulphite and dithionite, provided that the sum of the valencies of $A_m$ and $X_n$ is four.

2. A complex of claim 1 wherein m is 1.

3. A complex of claim 1 wherein A is 1,2-diaminocyclohexane.

4. A complex of claim 1 wherein A is 1,3-diaminopropane.

5. A complex of claim 1 wherein A is 1,2-diaminopropane.

6. A complex of claim 1 wherein A is 2,2'-bipyridine.

7. A complex of claim 1 wherein m is 2.

8. A complex of claim 1 wherein n is 2.

9. A complex of claim 8 wherein said monovalent anionic ligand is nitrate.

10. A complex of claim 1 wherein n is 1.

11. A palladium complex of claim 1 having the formula:

Pd(II)(cis-1,2-diaminocyclohexane)(NO$_3$)$_2$.

12. A palladium complex of claim 1 having the formula:

Pd(II)(trans-1,2-diaminocyclohexane)(NO$_3$)$_2$.

13. A palladium complex of claim 1 having the formula:

Pd(II)(cis-1,2-diaminopropane)(NO$_3$)$_2$.

14. A palladium complex of claim 1 having the formula:

(Pd)(II)(cis-1,3-diaminopropane)(NO$_3$)$_2$.

15. A complex of claim 1 having the formula:

Pd(II)(cis-2,2'-bipyridine)(NO$_3$)$_2$.

16. A palladium complex having the formula cis:

Pd(II)(NH$_3$)$_2$X wherein:
X is selected from the group consisting of divalent anionic ligands excluding oxalate and malonate.

17. A complex of claim 16 wherein said divalent anionic ligand is pyrophosphate or dithioxalate.

18. A palladium complex having the formula cis:

[Pd(II)A$_m$(OH)]$_x$X wherein m is 1 or 2,
x is 2, 3 or 4, and
when m is 1, A is selected from the group consisting of bipyridine and alkyl diamines other than ethylene diamine having the formula:

R$_1$RN—(Alk)—NRR$_1$ wherein R and R$_1$ may be the same or different and are H, $C_2$ to $C_6$ alkyl, $C_2$ to $C_6$ hydroxy alkyl, $C_2$ to $C_6$ alkoxy, $C_6$ to $C_{10}$ aryl, $C_3$ to $C_{12}$ cycloalkyl and $C_3$ to $C_{12}$ cycloalkenyl, and Alk is selected from the group consisting of unsubstituted $C_2$ to $C_{12}$ alkylene, $C_2$ to $C_{12}$ alkylene substituted with $C_2$ to $C_6$ hydroxy alkyl or $C_2$ to $C_6$ alkoxy; $C_6$ to $C_{10}$ aryl and $C_3$ to $C_{12}$ cycloalkane, and when m is 2, A is selected from the group consisting of $C_2$ to $C_6$ alkyl amine; $C_2$ to $C_6$ alkyl amine substituted in the alkyl group or nitrogen atom thereof by $C_2$ to $C_6$ hydroxy alkyl, hydroxy or $C_2$ to $C_6$ alkoxy; analine; benzyl amine and amino acids having the formula

R$^3$CHNH$_2$COOH wherein R$^3$ is H, $C_2$ to $C_6$ alkyl, $C_2$ to $C_6$ hydroxy alkyl and benzyl, and X represents two monovalent anionic ligands or one divalent anionic ligand when x is 2, three monovalent anionic ligands or one trivalent anionic ligand when x is 3, and four monovalent anionic ligands or two divalent anionic ligands when x is 4, with the provisos that
said monovalent anionic ligands are selected from the group consisting of chloride, bromide, iodide, nitrite, hydroxide, nitrate, lactate, $C_2$ to $C_6$ alkoxy, fluoride, acetate, trifluoroacetate, chloroacetate, cyanide, cyanate, thiocyanate, ozonide, azide, chlorite, hypochlorite and hypophosphite, and said divalent anionic ligands are selected from the group consisting of malonate, oxalate, pyrophosphite, dithiooxalate, phthalate, carboxyphthalate, gluconate, glucuronate, carbonate, sulphite, selenite, pyrosulphite, dithionite and sulphate, and said trivalent anionic ligands are selected from the group consisting of phosphate, arsenite, orthoarsenate and ferricyanide.

19. A complex of claim 18 wherein m is 1.

20. A complex of claim 18 wherein A is 1,2-diaminocyclohexane.

21. A complex of claim 18 wherein A is 1,3-diaminopropane.

22. A complex of claim 18 wherein A is 1,2-diaminopropane.

23. A complex of claim 18 wherein A is 2,2'-bipyridine.

24. A complex of claim 18 wherein m is 2.

25. A complex of claim 18 wherein m is 1.

26. A complex of claim 25 wherein said monovalent anionic ligand is nitrate.

27. A complex of claim 18 wherein x is 2.

28. A complex of claim 18 wherein x is 3.

29. A complex of claim 18 having the formula:

[Pd(II)(cis-1,2-diaminocyclohexane) (OH)]$_n$ [NO$_3$]$_n$ wherein: n=2, 3 or 4.

30. A complex of claim 19 having the formula:

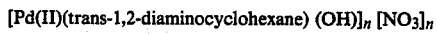
[Pd(II)(trans-1,2-diaminocyclohexane) (OH)]$_n$ [NO$_3$]$_n$ wherein: n=2, 3 or 4.

31. A palladium complex having the formula cis or trans:

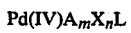
Pd(IV)A$_m$X$_n$L wherein
m is 1 or 2
n is 1, 2 or 4, and
when m is 1, A is selected from the group consisting of bipyridine and alkylene diamines having the formula

R$_1$RN—(Alk)—NRR$_1$ wherein R and R$_1$ may be the same or different and are H, C$_2$ to C$_6$ alkyl, C$_2$ to C$_6$ hydroxy alkyl, C$_2$ to C$_6$ alkoxy, C$_6$ to C$_{10}$ aryl, C$_3$ to C$_{12}$ cycloalkyl and C$_3$ to C$_{12}$ cycloalkenyl, and Alk is selected from the group consisting of unsubstituted C$_2$ to C$_{12}$ alkylene; C$_2$ to C$_{12}$ alkylene substituted with C$_2$ to C$_6$ hydroxy alkyl or C$_2$ to C$_6$ alkoxy; C$_6$ to C$_{10}$ aryl and C$_3$ to C$_{12}$ cycloalkane, when m is 2 A is two ligands selected from the group consisting of C$_2$ to C$_6$ alkyl amine; C$_2$ to C$_6$ alkyl amine substituted in the alkyl group or nitrogen atom thereof by C$_2$ to C$_6$ hydroxy alkyl, hydroxy or C$_2$ to C$_6$ alkoxy; aniline; benzylamine and amino acids having the formula

R$^3$CHNH$_2$COOH wherein R$^3$ is H, C$_2$ to C$_6$ alkyl, C$_2$ to C$_6$ hydroxy alkyl and benzyl, and X is a trivalent anionic ligand when n is 1, a divalent anionic ligand when n is 2 and a monovalent anionic ligand when n is 4;

L represents two monovalent anionic ligands when X is a divalent anionic ligand, and one monovalent anionic ligand when X is a trivalent anionic ligand, provided, that said monovalent anionic ligands are selected from the group consisting of chloride, bromide, iodide, nitrite, hydroxide, nitrate, lactate, C$_2$ to C$_6$ alkoxy, fluoride, acetate, trifluoroacetate, chloroacetate, cyanide, cyanate, thiocyanate, ozonide, azide, chlorite, hypochlorite and hypophosphite, said divalent anionic ligands are selected from the group consisting of malonate, oxalate, pyrophosphite, dithiooxalate, phthalate, carboxyphthalate, gluconate, glucuronate, carbonate, sulphite, selenite, pyrosulphite, dithionite and sulphate, said trivalent anionic ligands are selected from the group consisting of phosphate, arsenate, orthoarsenate and sulphate, and the sum of the valencies of A$_m$, X$_n$ and L is six.

32. A complex of claim 31 wherein m is 1.

33. A complex of claim 31 wherein A is 1,2-diaminocyclohexane.

34. A complex of claim 31 wherein A is 1,3-diaminopropane.

35. A complex of claim 31 wherein A is 1,2-diaminopropane.

36. A complex of claim 31 wherein A is 2,2'-bipyridine.

37. A complex of claim 31 wherein m is 2.

38. A complex of claim 31 wherein said monovalent anionic ligand is chloride, bromide, iodide, nitrite, hydroxide or nitrate.

39. A complex of claim 31 wherein said monovalent anionic ligand is nitrate.

40. A complex of claim 31 wherein said divalent anionic ligand is malonate, oxalate, pyrophosphate or dithioxalate.

41. A complex of claim 31 wherein said trivalent anionic ligand is phosphate.

42. A pharmaceutical composition is unit dosage form adapted for the treatment of animal tumor cells sensitive to the compounds represented by formulas V, VI and VII comprising an anti-tumor effective amount of a pharmaceutically acceptable carrier and at least one complex having one of the formulas;

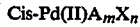
Cis-Pd(II)A$_m$X$_n$     (V)

wherein m is 1 or 2,
n is 1 or 2, and
when m is 1, A is selected from the group consisting of bipyridine and alkylene diamines other than ethylene diamine having the formula

R$_1$RN—(Alk)—NRR$_1$ wherein R and R$_1$ may be the same or different and are H, C$_2$ to C$_6$ alkyl, C$_2$ to C$_6$ hydroxy alkyl, C$_2$ to C$_6$ alkoxy, C$_6$ to C$_{10}$ aryl, C$_3$ to C$_{12}$ cycloalkyl and C$_3$ to C$_{12}$ cycloalkyl and Alk is selected from the group consisting of unsubstituted C$_2$ to C$_{12}$ alkylene; C$_2$ to C$_{12}$ alkylene substituted with C$_2$ to C$_6$ hydroxy alkyl or C$_2$ to C$_6$ alkoxy; C$_6$ to C$_{10}$ aryl and C$_3$ to C$_{12}$ cycloalkane, when m is 2, A is selected from the group consisting of C$_2$ to C$_6$ alkyl amine; C$_2$ to C$_6$ alkyl amine substituted in the alkyl group or nitrogen atom thereof by C$_2$ to C$_6$ hydroxy alkyl, hydroxy or C$_2$ to C$_6$ alkoxy; anailine; benzylamine and amino acids having the formula

R$^3$CHNH$_2$COOH wheren R$^3$ is H, C$_2$ to C$_6$ alkyl, C$_2$ to C$_6$ hydroxy alkyl and benzyl, and when n is 2, X is a monovalent anionic ligand selected from the group consisting of bromide, iodide, nitrite, hydroxide, nitrate, lactate, C$_2$ to C$_6$ alkoxy, fluoride, acetate, trifluoracetate, chloroacetate, cyanide, cyanate, ozonide, azide, chlorite, hypochlorite and hypophosphite, and when n is 1, X is a divalent anionic ligand selected from the group consisting of pyrophosphite, dithiooxalate, phthalate, carboxyphthalate, gluconate, glucuronate, carbonate, sulphite, selenite, pyrosulphite and dithionite, provided that the sum of the valencies of $A_m$ and $X_n$ is four;

$$cis\text{-}[PD(II)A'_m(OH)]_xX' \qquad (VI)$$

wherein m' is 1 or 2, x is 2, 3 or 4, and when m' is 1, A' is selected from the group consisting of bipyridine and alkyl diamines other than ethylene diamine having the formula:

$$R_1RN-(Alk)-NRR_1$$

wherein R, $R_1$ and Alk are as defined above, and when m' is 2, A' is selected from the group consisting of $C_2$ to $C_6$ alkyl amine; $C_2$ to $C_6$ akyl amine substituted in the alkyl group or nitrogen atom thereof by $C_2$ to $C_6$ hydroxy alkyl, hydroxy or $C_2$ to $C_6$ alkoxy; aniline; benzyl amine and amino acids having the formula $$R^3CHNH_2COOH$$

wherein $R^3$ is as defined above, and

X' represents two monovalent anionic ligands or one divalent anionic ligand when x is 2, three monovalent anionic ligands or one trivalent anionic ligand when x is 3, and four monovalent anionic ligands or two divalent anionic ligands when x is 4, with the provisos that said X' monovalent anionic ligands are selected from the group consisting of chloride, bromide, iodide, nitrite, hydroxide, nitrate, lactate, $C_2$ to $C_6$ alkoxy, fluoride, acetate, trifluoroacetate, chloroacetate, cyanide, cyanate, thiocyanate, ozonide, azide, chlorite, hypochlorite and hypophosphite, and said X' divalent anionic ligands are selected from the group consisting of malonate, oxalate, pyrophosphite, dithiooxalate, phthalate, carboxyphthalate gluconate, glucuronate, carbonate, sulphite, selenite, pyrosulphite, dithionite and sulphate, and said X' trivalent anionic ligands are selected from the group consisting of phosphate, arsenite, orthoarsenate and ferricyanide;

$$cis \text{ or trans } Pd(IV)A_o''X_p''L \qquad (VII)$$

wherein o is 1 or 2, p is 1, 2 or 4, and when o is 1, A'' is selected from the group consisting of bipyridine and alkylene diamines having the formula $$R_1-RN-(Alk)-NRR_1$$

wherein R, $R_1$ and Alk are as defined above, and when o is 2, A'' is two ligands selected from the group consisting of $C_2$ to $C_6$ alkyl amine; $C_2$ to $C_6$ alkyl amine substituted in the alkyl group or nitrogen atom thereof by $C_2$ to $C_6$ hydroxy alkyl, hydroxy or $C_2$ to $C_6$ alkoxy; analine; benzylamine and amino acids having the formula $$R^3CHNH_2COOH$$

wherein $R^3$ is as defined above, and

X'' is a trivalent anionic ligand when p is 1, a divalent anionic ligand when p is 2 and a monovalent anionic ligand when p is 4;

L represents two monovalent anionic ligands when X'' is a divalent anionic ligand, and one monovalent anionic ligand when X'' is a trivalent anionic ligand, provided, that said L monovalent anionic ligands are selected from the group consisting of chloride, bromide, iodide, nitrite, hydroxide, nitrate, lactate, $C_2$ to $C_6$ alkoxy, fluorite, acetate, trifluoroacetate, chloroacetate, cyanide, cyanate, thiocyanate, ozonide, azide, chlorite, hypochlorite and hypophosphite, said L divalent anionic ligands are selected from the group consisting of malonate, oxalate, pyrophosphite, dithiooxalate, phthalate, carboxyphthalate, gluconate, glucuronate, carbonate, sulphite, selenite, pyrosulphite, dithionite and sulphate, said L trivalent anionic ligands are selected from the group consisting of phosphate, arsenate, orthoarsenate and sulphate, and the sum of the valencies of $A_o''$, $X_p''$ and L is six.

43. A method for the treatment of animal tumor cells sensitive to complexes of the formula V, VI and VII of claim 42 comprising administering to an animal afflicted with said tumor cells an amount of a complex of formula (V), (VI) or (VII) effective to cause regression of said tumor.

44. A pharmaceutical composition as in claim 42 in which said compound is

Pd(II)(cis-1,2-diamocyclohexane)(NO$_3$)$_2$.

45. A pharmaceutical composition as in claim 42 in which said compound is

Pd(II)(trans-1,2-diaminocyclohexane(NO$_3$)$_2$.

46. A pharmaceutical composition as in claim 42 in which said compound is

Pd(II)(cis-1,3-diamopropane)(NO$_3$)$_2$.

47. A pharmaceutical composition as in claim 42 in which said compound is

Pd(II)(cis-2,2'-bipyridine)(NO$_3$)$_2$.

48. A pharmaceutical composition as in claim 42 in which said compound is

[Pd(II)(cis-1,2-diamocyclohexane)(OH)]$_n$[NO$_3$]$_n$ wherein n is 2, 3 or 4.

* * * * *